United States Patent
Halpern

(10) Patent No.: US 10,481,135 B1
(45) Date of Patent: Nov. 19, 2019

(54) SEPARATION DEVICES AND SENSORS INCLUDING TWO DIMENSIONAL MATERIALS THAT CHANGE PROPERTIES WHEN EXPOSED TO COMPONENTS SEPARATED FROM A SAMPLE

(71) Applicant: Joshua Halpern, Washington, DC (US)

(72) Inventor: Joshua Halpern, Washington, DC (US)

(73) Assignee: HOWARD UNIVERSITY, Washington, DC (US)

( * ) Notice: Subject to any disclaimer, the term of this patent is extended or adjusted under 35 U.S.C. 154(b) by 336 days.

(21) Appl. No.: 15/067,881

(22) Filed: Mar. 11, 2016

Related U.S. Application Data

(60) Provisional application No. 62/132,919, filed on Mar. 13, 2015.

(51) Int. Cl.
    *G01N 30/10* (2006.01)
    *G01N 30/76* (2006.01)
    *G01N 30/66* (2006.01)

(52) U.S. Cl.
    CPC ............. *G01N 30/10* (2013.01); *G01N 30/66* (2013.01); *G01N 30/76* (2013.01)

(58) Field of Classification Search
    CPC ......... G01N 30/10; G01N 30/76; G01N 30/66
    See application file for complete search history.

(56) References Cited

U.S. PATENT DOCUMENTS

| 7,612,551 | B2 | 11/2009 | Mihaila |
| 7,956,427 | B2 | 6/2011 | Lieber et al. |
| 8,012,420 | B2 | 9/2011 | Ramamurthy et al. |
| 8,105,538 | B2 | 1/2012 | Ramamurthy et al. |
| 8,232,584 | B2 | 7/2012 | Lieber et al. |
| 2002/0088753 | A1* | 7/2002 | Huber .................. B01D 15/366 210/656 |
| 2011/0011157 | A1* | 1/2011 | Bourlon ................. B01J 20/205 73/23.41 |

OTHER PUBLICATIONS

Sakhaee-Pour et al. "Applications of single-layered graphene sheets as mass sensors and atomistic dust detectors", Solid State Communications 145 (2008) 168-172, Oct. 2017, see attached publication.*
Chen et al. "Sub-ppt gas detection with pristine graphene", 2012 American Institute of Physics, see attached publication.*
Chen, G., et al.; "Sub-ppt gas detection with pristine graphene"; Applied Physics Letters; vol. 101, No. 5, 053119; 2012.

(Continued)

*Primary Examiner* — Xin Y Zhong
(74) *Attorney, Agent, or Firm* — Sughrue Mion, PLLC

(57) ABSTRACT

A device and method for the separation, detection, and identification of multiple individual components in a sample where the separation device is gas chromatograph or a microchip separation device. The chromatograph or microchip separation and detection device has a detector including a two dimensional or substantially two dimensional sensor material sensitive to and has a property change (such as a change in resistance) when the surface of the two dimensional or substantially two dimensional sensor material is exposed to a component of a sample in amounts as low as $10^{-21}$ grams of component.

24 Claims, 2 Drawing Sheets

(56) References Cited

OTHER PUBLICATIONS

Garcia, N.; "Sandia's lab on a chip to spot chemical clues"; News Release; Sandia National Laboratories; Apr. 23, 1998; 4 pages.
Jensen, K., et al.; "An atomic-resolution nanomechanical mass sensor"; Nature Nanotechnology; vol. 3, pp. 533-537; 2008.
Nomani, MD W.K., et al.; "Highly sensitive and multidimensional detection of NO2 using In2 O3 thin films"; Sensors and Actuators B: Chemical; vol. 160, No. 1, pp. 251-259; 2011.
Schedin, F., et al.; "Detection of Individual Gas Molecules Adsorbed on Graphene"; Nature Materials; vol. 6, No. 9, pp. 652-655; 2007.
Wikipedia contributors; "Boron nitride"; Wikipedia, The Free Encyclopedia; Accessed Jul. 18, 2013; 11 pages.
Wikipedia contributors; "Graphite oxide"; Wikipedia, The Free Encyclopedia; Accessed Jul. 18, 2013; 8 pages.
Wikipedia contributors; "Lab-on-a-chip"; Wikipedia, The Free Encyclopedia; Accessed Nov. 11, 2013; 3 pages.
Wikipedia contributors; "Molybdenum disulfide"; Wikipedia, The Free Encyclopedia; Accessed Jul. 18, 2013; 5 pages.
Zhao, Lifang, et al., "Ionic Liquid Functionalized Graphene Based Immunosensor for Sensitive Detection of Carbohydrate Antigen 15-3 Integrated with Cd2+-Functionalized Nanoporous TiO2 As Labels." Biosensors and Bioelectronics, vol. 59, Sep. 15, 2014, pp. 75-80, Abstract only.
Pre-Filing Search (No. 1), dated at least prior to Mar. 13, 2015, 95 pages.
Pre-Filing Search (No. 2), dated at least prior to Mar. 13, 2015, 64 pages.

\* cited by examiner

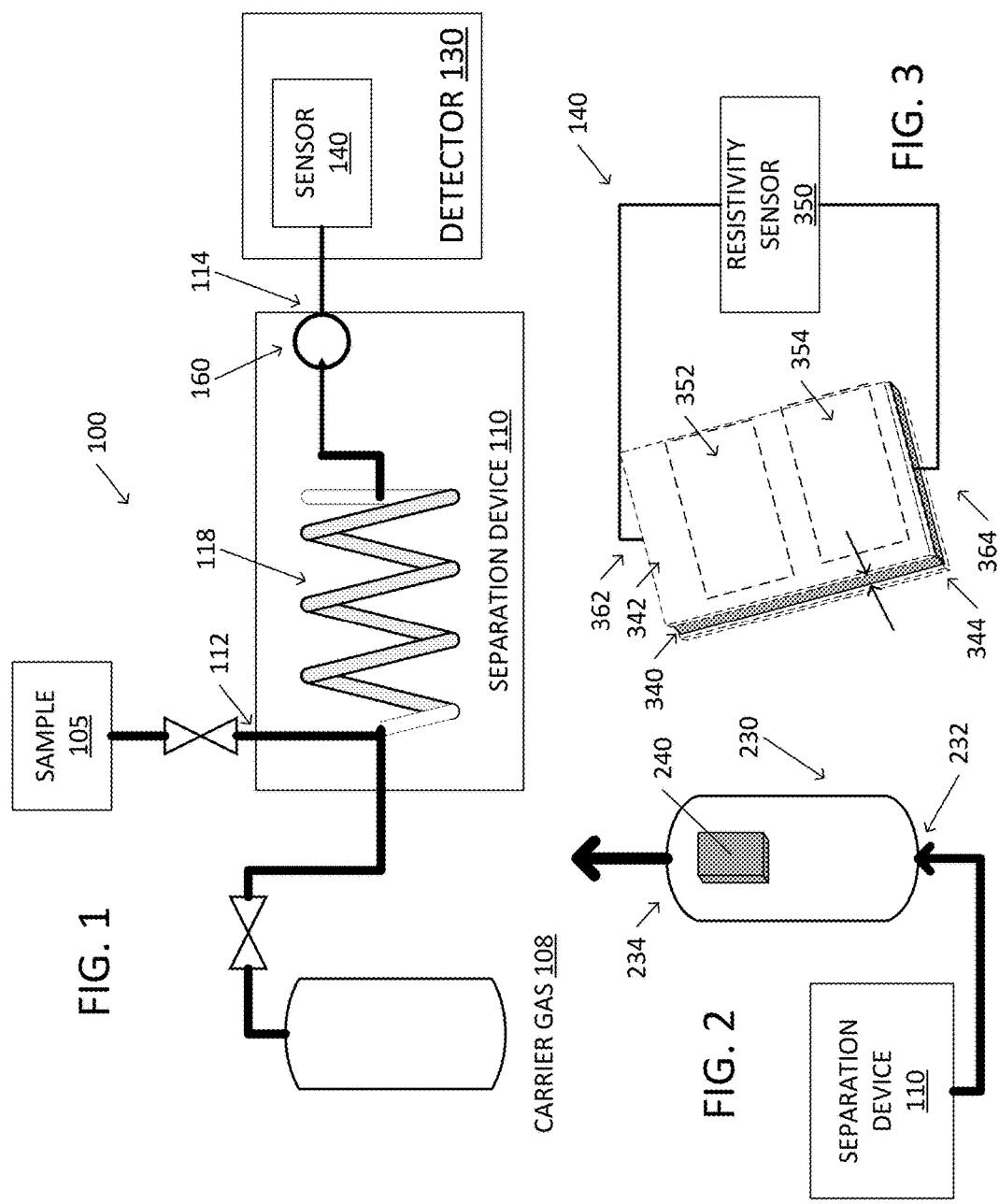

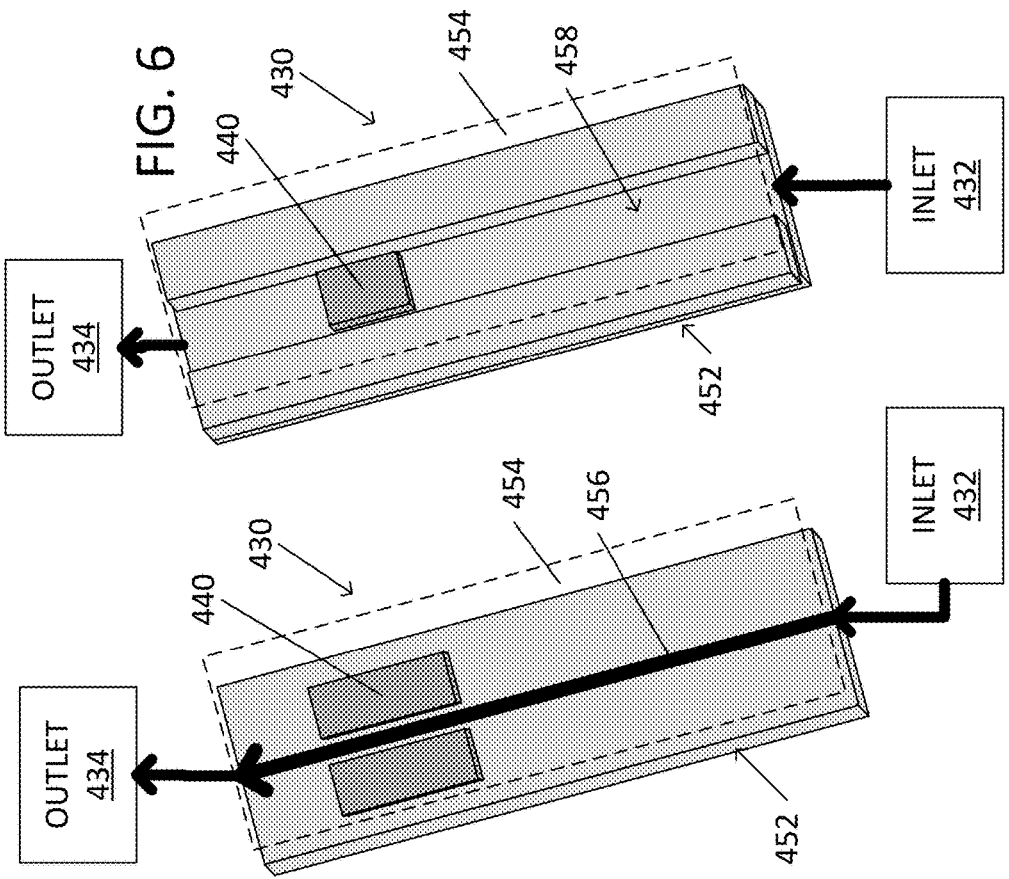
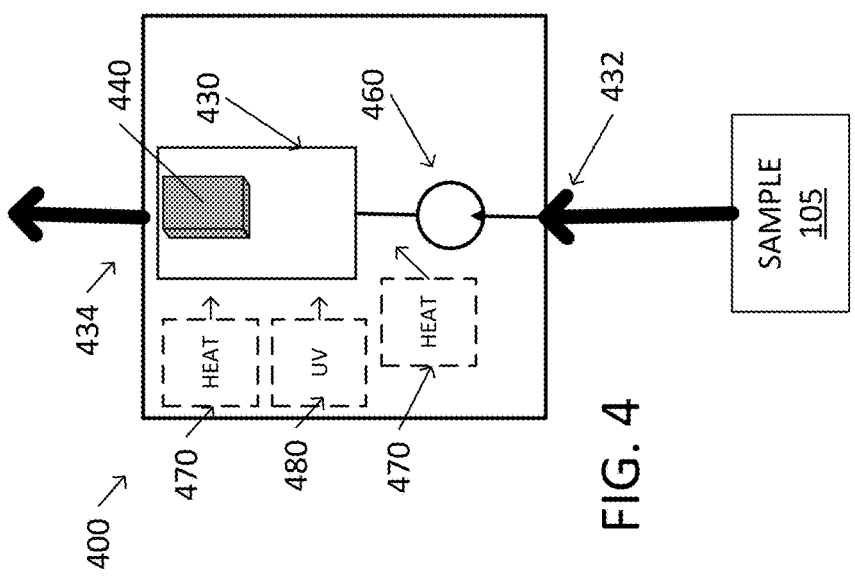

SEPARATION DEVICES AND SENSORS INCLUDING TWO DIMENSIONAL MATERIALS THAT CHANGE PROPERTIES WHEN EXPOSED TO COMPONENTS SEPARATED FROM A SAMPLE

RELATED APPLICATION(S)

This application claims the benefit of U.S. provisional patent application No. 62/132,919 filed Mar. 13, 2015, the contents of which are incorporated by reference in its entirety.

FIELD

This application is directed to detection and separation devices that include one or more of a two dimensional or a substantially two dimensional material the surface of which is highly sensitive to components of a sample. The devices described herein include, but are not limited to, (1) gas chromatographs which include a detection device which includes a two dimensional or a substantially two dimensional material, (2) gas chromatographs which have a stationary phase incorporating a two dimensional or a substantially two dimensional material and a detection device which also includes such materials, or (3) a micro-electro-mechanical system (MEMS) device that includes a two dimensional or a substantially two dimensional material and a detection device which also includes such materials.

BACKGROUND

Gas chromatography is used for separating and analyzing compounds that can be vaporized without decomposition. Gas chromatography may be used to test compound purity, separate different compounds in a blend, or aid in compound identification.

A gas chromatograph has a mobile or moving phase which is an inert carrier gas. The gas chromatograph also has a stationary phase which is a material on an inert solid support inside a tube or column. The compound(s) in or components of a sample being analyzed or separated are injected into the chromatograph system, converted into a gas (if not already a gas), and transported to the column or tube where the analyte interacts with the stationary phase in the column. The compound(s) in the injected sample flow through the column with a carrier gas and are eluted at different times as a function as how they are retained by the stationary phase in the column. A comparison of retention times, which are a function of the physical properties of the column and components of the sample, provide a way to analytically identify and separate compounds or components in the sample. Generally substances are qualitatively identified by the order in which they emerge (elute) from the column and by the retention time of the component in the column. As the separated volatilized chemical components exit the end of the column, they are detected with a sensor/detector and identified. In addition to the physical properties of the column and the compound in the sample, parameter such as carrier gas, flow rate, column length, and temperature of the various components of the chromatographic system can also affect the retention time of the eluates.

There can be a wide range of carrier gases. These gases can include hydrogen and helium. Helium is non-flammable and works with a great number of sensors/detectors and as a result is one of the most common carrier gases used.

Technology sometimes referred to as lab-on-a-chip also exists for the separation and analysis of very small amounts of gases and/or liquids. Minute amounts of gases or liquids may be separated and analyzed by putting the gas or liquid through microchip channels having diameters of from about 10 µm to 100 µm. In the channels, retention times of different components of a sample are not the same because of a difference in affinities to a stationary phase.

Separation of very small samples into their minute components, detection, identification of, and determination of the relative amounts of components in extremely small liquid or gas samples and/or components is a challenging problem.

Gas chromatography systems use sensors to determine when a gaseous component of a sample is exiting the column. Common sensors include flame ionization sensors, thermal conductivity sensors, and mass spectrometers. Thermal conductivity sensors can be used to detect components other than the carrier gas when their thermal conductivities are different from that of the carrier gas at the operation temperatures of the gas chromatograph. Flame ionization sensors generally are more sensitive to hydrocarbons than thermal conductivity sensors but cannot detect water or other completely oxidized molecules. They require a supply of flammable gas (usually hydrogen). Mass spectrometers detect the ionic masses of the product after ionization and are complex and large.

There is always a need for sensors and detectors that include the latter sensors with higher sensitivity and sensitivity to a broad range of compounds. In addition, simplicity of design and operation, economy of operation in terms of cost and materials, small sensor size, and the simplicity of integrating the sensor into field and process instrumentation are important. This is particularly the case for MEMS devices used for separation in volumes as low as a picoliter or less.

Full sized gas chromatographs and implementation of separation and detection devices on MEMS devices can provide data in the form of graphs or "chromatograms" of sensor/detector responses (generally the y-axis) against retention time (generally the x-axis). Chromatographs and MEMS devices provide a spectrum of peaks representing the components in a sample moving through and exiting from the column or chip at different times. The time a component of a sample is retained in a column or chip can be used to identify the component when conditions are constant. Areas under the peaks are proportional to the amounts of sample components moving through the chromatograph or chip; hence, using these areas permit the determination of relative amounts of components in the sample. The concentration of a component in a sample can be determined by measuring the response for a series of concentrations of the component of interest or by determining the relative response factor of the component which the expected ratio of a component to a standard put through the chromatograph. The response factor is calculated by determining the response of a known amount of component and a constant amount of chemical added to the sample at a constant concentration that has a distinct retention time relative to the component of interest.

The ultimate goal of any chromatographic separation, microchip separation using a MEMS device, or spectrographic method and analysis is to achieve the greatest level of sensitivity that is possible to determine if and what amounts of each components of a sample are present. There are three principal advantages of using the proposed sensor in chromatography. First, the two dimensional sensors (TDS) described herein are much more sensitive to at least some eluting molecules, even below a pico gram (pg) limit. Second, the electrical and materials requirement of the TDS are very low; a few microamp source or a constant voltage source are all that is required beyond those for the chromatographic system itself. This is important for field measurements where easy access to electricity and/or gases may be limited. Third, the size of the two dimensional sensor, which includes the two dimensional material or substantially two dimensional material and/or detector that includes the two dimensional sensor, may be on a micrometer scale. TDS can be 10 µm$^2$ to 100 µm$^2$ on a side. Thus, TDSs are inherently good matches to MEMS scale chromatographs. Various detectors and their detection limits are described in the table below.

| Type of Detector | Applicable Samples | Detection Limit |
|---|---|---|
| Mass Spectrometer (MS) | Tunable for any sample | .25 to 100 pg |
| Flame Ionization (FID) | Hydrocarbons | 1 pg/s |
| Thermal Conductivity (TCD) | Universal | 500 pg/ml |
| Electron-Capture (ECD) | Halogenated hydrocarbons | 5 fg/s |
| Atomic Emission (AED) | Element-selective | 1 pg |
| Chemiluminescence (CS) | Oxidizing reagent | Dark current of PMT |
| Photoionization (PID) | Vapor and gaseous Compounds | .002 to .02 µg/L |

An ultimate goal with the chemical sensors described herein is to determine even if one atom or molecule and/or $10^{-21}$ grams of a sample are present as a component of a multicomponent sample under analysis. Such sensitivities have been demonstrated, but not in conjunction with chemical separation systems such as gas chromatographs. This is not currently possible with known chromatograph sensors. Two dimensional and substantially two dimensional materials such as graphene, graphene oxide (also known as graphite oxide), two dimensional boron nitride (BN) or boron nitride nanotubes, and two dimensional molybdenum disulfide ($MoS_2$) can provide a detectable change in electron transport properties, such as a change in electrical resistance or the frequency of a surface oscillation, without or with very low intrinsic noise which permits measurement of the change(s) in resistance or other property effected by adsorption of $10^{-21}$ grams of elute and by even one molecule on the surface of a sensor including the two dimensional or substantially two dimensional material as described herein.

Schedin et al., in Nature Materials 6, 652-655 (2007) describe detection of individual gas molecules adsorbed on graphene measuring Hall resistivity by a 10 Tesla magnetic field. The Schedin article describes the detection of an individual gas and the determination of the concentration of the gas by reference to a standard. Simple resistance measurements have demonstrated detectivity of 10 ppb. However, no publication discusses coupling the detector with a separation device such as a gas chromatograph. Separation, detection and identification of a plurality of very small individual components in a multi-component sample by a two dimensional or substantially two dimensional material in a stationary phase and/or sensor is not described or suggested.

At present gas chromatograph systems or MEMS devices are not known that separate components of a sample and then utilize a sensor and/or stationary phase for separation where the system and devices include sensors and stationary phases that utilize two dimensional or substantially two dimensional materials. The approach described herein provides a detection device whose sensitivity matches or exceeds those in general use, is compact, is energy efficient, and integrates with MEMS scale separation and detection devices. The approaches described herein are novel because they have the potential to greatly increase the sensitivity of gas chromatography to detect individual gas molecules (1) using simple resistivity measurements such as Hall resistivity measurements, (2) using surface acoustic wave sensors which include graphene (or other two dimensional or substantially two dimensional materials as described herein), and (3) using nano-mechanical resonator measuring devices in combination with the two dimensional or substantially two dimensional materials. All of the latter are also easily integratable with MEMS scale separation devices. The applications for the devices described herein are far reaching. Small devices can be used in well drilling, exploration probes, sensing environments in inconvenient places, separating and identifying low levels of deleterious substances in mixtures of gases (such as separation and identification with gas masks), and other analytical (qualitatively and quantitative) and biomedical applications.

SUMMARY

To solve the above problems in respect to the detection, separation, and identification of small amounts of multiple individual components in a sample, described herein is a (1) detection and separation device such as gas chromatograph or a microchip separation device where the chromatograph or microchip separation and detection device has a sensor which includes a two dimensional or substantially two dimensional sensor material which is sensitive to and has a property change (such as a change in resistance) when the surface of the two dimensional or substantially two dimensional sensor material is exposed to a volatilized component of a sample having a plurality of components; or (2) a gas chromatograph which includes a two dimensional or substantially two dimensional material in its stationary phase and sensor; or (3) a MEMS or microchip separation and detection device capable of separating and analyzing a very small amount of volatilized or liquid sample emerging from the MEMS device where the MEMS device has a sensor and stationary phase which includes a two dimensional or substantially two dimensional material. Accordingly, provided herein is a gas chromatograph or a microchip separation and detection device configured to separate a gas or liquid sample into its individual components and then detect the individual components less than one pico gram (pg) in the sample that have been separated into components by a column in the chromatograph or a microchip configured to separate a volatized material or small amounts of liquid material.

In one aspect the detection device includes the sensor and measuring device used in conjunction with the two or substantially two dimensional material. The measuring device affects how much of the sensitivity of the two or substantially two dimensional can be utilized by the detection device. Conductivity changes can be determined for components comprising from about 3 to about 10 parts per billion (ppb) of a sample. Surface acoustical wave (SAW) measuring devices where an electrical oscillator(s) on the surface of the two or substantially two dimensional material measure shifts in acoustical waves, which shifts then are translated into electrical signals, can be used to detect and measure components comprising about 2 to about 3 ppb of a sample. Nano-mechanical resonating devices may be used in conjunction with the two or substantially two dimensional material to measure components comprising as low as $10^{-21}$ grams of a sample. Surface acoustical wave and nanomechanical resonating devices are particularly useful because they operate at high frequencies where low frequency noise (1/f noise where f is less than about 10 to about 20 kHz) is not detected.

In one aspect, the gas chromatograph and/or microchip separation device includes at least one inlet configured to receive a volatizable liquid or gas sample; at least one heated chamber configured to volatize the received liquid sample; and an outlet downstream the inlet the sensor and detection device downstream the inlet near the outlet.

In the gas chromatograph aspect, a stationary phase includes a material on an inert solid support inside a tube or column which is upstream the detection device and sensor which includes the two dimensional or substantially two dimensional material. The column, through which a volatilized sample is moved with a carrier gas, has a stationary phase material, such as activated charcoal or the two or substantially two dimensional material; has at least one inlet configured to receive at least a portion of the volatilized sample; and at least one detection device downstream the inlet and at about the outlet which has a sensor configured to detect the at least one portion of the volatilized sample, the sensor including at least one substantially two dimensional material whose conductivity or other properties associated with electron transport changes from a normalized baseline value, when as little as one pico gram of sample contacts the surface of the two dimensional or substantially two dimensional material. Further the properties of the two dimensional or substantially two dimensional materials can be returned to or maintained at a baseline where the sensitivity is highest for measurement utilizing conductivity, SAW devices or resonator devices either by heating, exposure to UV light, chemical cleaning or simply waiting until the adsorbed molecules vaporize. In the aspect where the separation device includes a microchip configured to separate very small amounts of volatilized gas or liquids, the microchip device includes channels having diameters of 10 µm to 100 µm In an important aspect, the sensor has a two dimensional or substantially two dimensional planar array of atoms where the planar array is provided by a compound which is selected from the group consisting of graphene, graphene oxide (also known as graphite oxide), boron nitride (BN), boron nitride nanotubes, molybdenum disulfide (MoS2) and mixtures thereof, or other two dimensional materials, the entire latter group being two dimensional or substantially two dimensional.

The sensors which form part of the detection and separation device include a two dimensional or substantially two dimensional material configured to detect a change of a property at least 3% from a standard, such as electrical resistance or current, in response to being exposed to a sample material having multiple components emerging from the gas chromatograph or microchip separation device. These two dimensional materials or substantially two dimensional materials are selected from the group consisting of graphene, graphene oxide (also known as graphite oxide), boron nitride (BN), boron nitride nanotubes, molybdenum disulfide (MoS2) and mixtures thereof, or other two dimensional materials. In a very important aspect, the atoms of the two dimensional material are in a planar array of a single layer of atoms such as hexagonal ring of carbon atoms in graphene.

In another aspect, the chromatograph, detection devices and sensors which form a part of the detection devices are very small and especially useful with equipment which is to detect chemicals in very confined spaces. In this case, the microchips may be generally not larger than about a square millimeter although for particular applications the size may be larger and the sensors are generally sheet-like or planar and may be as small as 10 µm2 to 100 µm2 on a side and work in combination with a microchip no larger than about 1 µm2 to about 100 µm2, preferably about 50 µm2.

Also described herein is a method for separating, detecting, identifying and determining relative amounts of components in a very small multicomponent sample by using the two dimensional and/or substantially two dimensional sensor material described above which is sensitive to and will a change in one or more properties which is a function of the compound or component emerging from a gas chromatograph or microchip. The property change being effected is at least 3% from a measured standard, such as electrical resistance or current, resulting from as low as one pico gram (or even less such as 10-21) grams of a component, or even as low as one molecule of nitric oxide, or where the component does not form more than 3 ppb of the sample.

BRIEF DESCRIPTION OF THE DRAWINGS

FIG. 1 includes a block diagram of an example detection and separation device in accordance with various embodiments.

FIG. 2 includes a block diagram of an example portion of detection and separation device including a column in accordance with various embodiments.

FIG. 3 includes a block diagram of a portion of an example sensor in accordance with various embodiments.

FIG. 4 includes a block diagram of an example microchip detection and separation device in accordance with various embodiments.

FIG. 5 includes a block diagram of an example sensor implementation in accordance with various embodiments.

FIG. 6 includes a block diagram of another example sensor implementation in accordance with various embodiments.

DETAILED DESCRIPTION

A two dimensional material is a compound with a two dimensional structure, e.g., a compound such as graphene which is a sheet formed from atoms, such as carbon atoms which are in a generally planar layer one atom thick. The two dimensional material will have a property, for example an electron transport property (such as electrical resistance), which will change at least 3% when the surface of the material is exposed to as low as one pico gram (or even less such as $10^{-21}$) grams of analyte, or even as low as one molecule of nitric oxide.

A substantially two dimensional structure has more than one layer or where there is one layer of atoms sandwiched between another layer of different atoms, such as occurs with molybdenum disulfide. A substantially two dimensional material with a substantially two dimensional structure will change a property, for example an electron transport property (such as resistance), at least 3% when the surface of the material is exposed to one pico gram of a component of a sample, or in the alternative is exposed to one molecule of analyte nitric oxide.

The structure of graphene is a planar sheet of one-atom-thick planar sheets of carbon atoms in six carbon membered hexagon rings in a honeycomb lattice of the six membered rings sharing carbon atoms.

Graphene oxide is in the form of layer(s) of molecular sheets which include carbon, oxygen, and hydrogen with carbon to oxygen ratios of about 2.1 to about 2.9. It can have epoxide groups, carbonyl groups (C=O), hydroxyl (—OH), carboxyl, and phenol groups attached to sides of the sheet. There may be some buckling or deviation from the planarity of the "sheets" which form layers of about 1.1±about 0.2 nm thick. The edges of each layer may be terminated with carboxyl and/or carbonyl groups.

Molybdenum disulfide has a structure where Mo(IV) is in a trigonal prismatic coordination sphere being bound to six sulfide type ligands. The sulfur center is pyramidal and is connected to three Mo centers. Trigonal prisms are interconnected to give a layered structure where molybdenum atoms are sandwiched between layers of sulfur atoms. Weak van der Waals interactions between sheets of sulfide atoms provide the sheet(s) of molybdenum disulfide.

Boron nitride for the sensors described herein has a hexagonal form in sheets with a structure similar to graphene with hexagonal rings and make take the form of a nanotube. The layers may be held together by van der Walls forces. The sheets are not completely planar as the boron atoms lying in a different plane than the nitrogen atoms.

In an important aspect, the above two dimensional and substantially two dimensional sheets of materials have low frequency noise, commonly referred to as 1/f noise, as an intrinsic property where f is less than about 10 to about 20 kHz. In an important aspect, when the same material is not two dimensional or substantially two dimensional, but rather is in the form of a nanotube, the two dimensional or substantially two dimensional sheet material should exhibit noise of a magnitude which is less than three or more times the noise level of the same material in the form of a nanotube. This property is very important to the identification and determination of amounts of components in a sample. This problem may be minimized by using changes in the frequency of surface acoustic waves above 100 kHz in surface acoustic wave (SAW) devices based on graphene.

With referent to FIG. 1, an example of the detection and separation device 100 described herein is illustrated and configured to separate and detect multiple individual components in a sample 105. The device 100 includes a separation device 110 having at least one inlet 112 configured to receive the sample 105 and at least one outlet 114 configured to permit the outflow of individual components of the sample 105 from the separation device 110; and at least one detector 130 configured to detect at least one of the multiple individual components of the sample 105 when at least one of the individual multiple components a liquid or is volatilized. The detector 130 has at least one sensor 140, which includes at least one material selected from the group consisting of a two dimensional material, a substantially two dimensional material, and combinations thereof. These materials have a property that will change at least 3% when a surface of the material is exposed to one pico gram of a volatilized component of a sample. In an important aspect the materials are selected from the group consisting of two dimensional or substantially two dimensional graphene, two dimensional or substantially two dimensional graphene oxide, two dimensional or substantially two dimensional boron nitride, two dimensional or substantially two dimensional molybdenum disulfide, and combinations thereof.

As described herein, in one aspect the device 100 may be a gas chromatograph wherein the separate device 110 includes at least one heated chamber 118 configured to volatize a received sample 105 to provide a volatilized sample. Referring to FIG. 2, the gas chromatograph includes at least one column 230 configured to hold a stationary phase material 240 through which the volatilized sample is moved with a carrier gas 108. The column 230 includes at least one inlet 232 configured to provide ingress and an outlet 234 which provides egress from the at least one column 230 for at least a portion of the volatilized sample. The detector 130, including the sensor 140 having the two or substantially two dimensional material, is downstream from the inlet 232 and is near the outlet 234. In an important aspect, the column 230 includes a stationary phase material 240, which comprises the two or substantially two dimensional material.

Certain embodiments of the sensor 140 are illustrated in FIG. 3. The sensor 140 includes the two or substantially two dimensional material 340 having a thickness (between the arrows) of about one atom or, depending on the embodiment, one layer having about a one atom thickness sandwiched between other layers 342 and 343 as described herein. The sensor 140 material 340 is electrically connected using conventional methods to circuitry used to monitor a characteristic that changes in response to exposure to (or engagement with) individual components of the sample 105. For example, a resistivity sensor 350 as known in the art can be connected to the material 340 to continuously monitor the material's resistivity, which changes at least 3% in response to exposure to certain components. The resistivity sensor 350 may be connected to other circuitry (not shown) to record or display such changes to monitor the results of what is detected from the sample.

In another aspect, the detection and separation device includes a microchip device 400 with a detector 430 with the sensor 440 as described herein. In this aspect the microchip device 400 has at least one inlet 432 configured to receive the sample 105 and at least one outlet 434 configured to permit the outflow of individual components of the sample 105 from the microchip device 400. In this approach, the detector 430 has a sensor 440, which includes materials selected from the group consisting of two dimensional or substantially two dimensional graphene, two dimensional or substantially two dimensional graphene oxide, two dimensional or substantially two dimensional boron nitride, two dimensional or substantially two dimensional molybdenum disulfide, and combinations thereof. In an important aspect illustrated in FIGS. 5 and 6, the microchip device 400 includes a silicon chip substrate 452 and a second planar substrate 454 with the two dimensional or substantially two dimensional material 440 sandwiched in between the substrates. Channels 456, 458 are etched in the silicon (see channel 458 of FIG. 6) and/or the two dimensional or substantially two dimensional material (see channel 456 of FIG. 5).

In its least sensitive form, the detector will measure a property which will change at least 3% when the material is exposed to a component forming not more than about 10 ppb of the sample, or even as low as one pico gram of a sample. Sensitivity will be affected by the measuring device of the detector. While the sensor in special configurations will be able to "sense" components of a sample comprising $10^{-21}$ grams of the sample, a detector which simply measures conductivity may measure components forming 10 ppb of a sample. Optionally, with referent to FIG. 3, one or more SAW measuring devices 352 may be included, in which case an electrical oscillator(s) on the surface of the two or substantially two dimensional material measure shifts in acoustical waves, which shifts then are translated into electrical signals that can be used to detect and measure components comprising about 2 to about 3 ppb of a sample. In another optional aspect, one or more cryogenically cooled nano-mechanical resonating devices 354 may be used in conjunction with the two or substantially two dimensional material to measure components comprising as low as $10^{-21}$ grams of a sample.

The separation and detection device also includes a pump 160, 460, such as a diaphragm pump, to create a positive pressure to push the sample 105 and carrier gas 108 or media through the column 130 or channels 456, 458 of the microchip 400. The separation and detection device also may include one or more heaters 470 and/or UV light sources 480 positioned to expose the stationary phase/sensor 140, 240, 340, and/or 440 and/or detector 430 to heat or UV light. The heaters 470 are positioned to volatilize materials going through the gas chromatograph or microchip separation and detection device to permit the device to receive a gas in the stationary phase. The heater 470 also may be positioned to heat the two dimensional or substantially two dimensional material to clean that material which forms a part of the detector/sensor and/or the stationary phase. In an important aspect, the two dimensional and/or substantially two dimensional material is mounted on a substrate 452, 454 (as a part of the "sandwich" structure described above) that is substantially transparent to UV light. This material can be polycarbonate, polymethylmethacrylate (PMM) and cyclo olefins and any other material that permits sufficient UV light, such as from a light emitting diode, to be transmitted to the surface of the two dimensional or substantially two dimensional material 440. The UV light cleans the latter material in the stationary phase or sensor by breaking bonds between the components of the sample and the two dimensional and/or substantially two dimensional material. Using heat or UV light permits constant cleaning which maintains sensitivity of the sensor and detector as well as the stationary phase so that neither the sensor nor stationary phase will not saturate with the materials being analyzed. Hence minimum concentrations can be separated and detected, sensitivity is maintained and minimum masses of individual components can be detected. By cleaning the stationary phase, the rate that material can be put through a small microchip separation and detection device can be maintained and/or increased.

The microchip separation and detection device can be fabricated by depositing the two dimensional material or substantially two dimensional material on a substrate such as silicon, polycarbonate, PMMA or cyclic olefin. Thereafter the channels are etched into the two dimensional material or substantially two dimensional material. The substrate with the etched channels 456, 458 may be mounted on a silicon chip to create a "sandwich" with the two dimensional or substantially two dimensional material in the middle. The channels 456, 458 should be linear or straight so there will not be resistance to the flow of the sample through the channels 456, 458. The detector will have the two dimensional or substantially two dimensional material between two contacts 362, 364 as illustrated in FIG. 3 to receive electrical signals through the contacts 362, 364.

The separation and detection devices described herein also are used in a method to detect, separate and identify at least one component of a multicomponent sample. The method for detecting and separating components of a sample having multiple individual components comprises transporting a sample through a separation device having at least one inlet configured to receive the sample and a at least one outlet configured to permit the outflow of the multiple individual components of the sample from the separation device; and impinging the multiple individual components of the sample onto at least one sensor configured to detect individual components of the sample, the at least one sensor including at least one material selected from the group consisting of a two dimensional material, a substantially two dimensional material and combinations thereof, the sensor sensing a property which changes at least 3% when the material is exposed to a component forming not more than about 10 ppb of the sample. The sensitivity to smaller components can be achieved with measuring devices which measures conductivity, which are a surface acoustical wave measuring devices, or which are a nano-mechanical resonator measuring devices described above. Hence using the method, individual components comprising one picoliter, one picogram or even as low as $10^{-21}$ grams of the sample can be separated and detected. The method described herein also permits the determination of relative amounts of components in the multi-component sample.

What is claimed is:

1. A detection and separation device configured to separate and detect multiple individual components in a sample, the device comprising:
    a separation device having at least one inlet configured to receive the sample and at least one outlet configured to permit outflow of the multiple individual components of the sample from the separation device; and
    at least one detector comprising at least one sensor configured to detect volatilized components of the sample when the sensor is exposed to an individual component received from the separation device, the sensor including at least one material selected from the group consisting of a two dimensional material, a substantially two dimensional material, and combinations thereof, the sensor having one or more channels formed in the at least one material, the sensor configured to sense a property which changes at least 3% when the at least one material is exposed to a component forming not more than about one pico gram of the sample, and the sensor configured to sense a property which changes at least 3% when the at least one material is exposed to a component forming not more than about 3 ppb of the sample.

2. The detection and separation device recited in claim 1, wherein the sensor is configured to detect multiple ones of the multiple individual components of the sample and to detect at least one of the individual components which forms not more than about one picoliter of the sample.

3. The detection and separation device recited in claim 1, wherein the sensor is configured to detect multiple ones of the multiple individual components of the sample and to detect at least one of the individual components which forms not more than about $10^{-21}$ grams of the sample.

4. The detection and separation device recited in claim 1, wherein the material is selected from the group consisting of two dimensional or substantially two dimensional graphene, two dimensional or substantially two dimensional graphene oxide, two dimensional or substantially two dimensional boron nitride, two dimensional or substantially two dimensional molybdenum disulfide, and combinations thereof.

5. The detection and separation device recited in claim 1, wherein the material is two dimensional graphene, substantially two dimensional graphene, or a combination thereof.

6. The detection and separation device recited in claim 1, comprising a gas chromatograph comprising at least one heated chamber configured to volatize the sample to provide a volatilized sample; and at least one column downstream the inlet, wherein the column is configured to hold a stationary phase material through which the volatilized sample is moved with a carrier gas, the column including at least one outlet downstream the inlet, the outlet configured to provide egress from the at least one column for at least a portion of the volatilized sample, the detector being downstream from the inlet.

7. The detection and separation device in claim 1, wherein the detection and separation device comprises a channel which comprises a stationary phase including at least one of the two dimensional or substantially two dimensional material between the inlet and the outlet, and wherein the sensor is downstream of the inlet.

8. The detection and separation device in claim 1, wherein the device is in the configuration of a microchip and the sensor has a surface area of about 10 µm$^2$ to about 100 µm$^2$.

9. The detection and separation device in claim 8 wherein the microchip is not larger than about one square millimeter.

10. The detection and separation device in claim 1, wherein the detector comprises at least one measuring device which measures conductivity, which is a surface acoustical wave measuring device or a nano-mechanical resonator measuring device.

11. A microchip detection and separation device configured to separate and detect multiple individual components in a sample, the microchip comprising:
  a separation device having at least one inlet configured to receive the sample and at least one outlet configured to permit the outflow of the multiple individual components of the sample, and channels between the inlet and the outlet, the channels having at least one diameter in the range of from about one micron to about one millimeter; and
  at least one sensor configured to detect at least one of the multiple individual components of the sample when at least one of the individual multiple components is volatilized or is a liquid, the sensor including at least one channel formed in at least one material selected from the group consisting of a two dimensional material, a substantially two dimensional material and combinations thereof, the sensor having a sensing property which changes at least 3% when the material is exposed to a component forming not more than about one pico gram of the sample, and the material is configured to detect multiple individual components of the sample and is capable of detecting at least one of the individual components which form not more than about 1 pico gram of the sample.

12. The microchip detection and separation device of claim 11 wherein the material is selected from the group consisting of two dimensional or substantially two dimensional graphene, two dimensional or substantially two dimensional graphene oxide, two dimensional or substantially two dimensional boron nitride, two dimensional or substantially two dimensional molybdenum disulfide, and combinations thereof.

13. The microchip detection and separation device recited in claim 11, wherein the material is two dimensional graphene, substantially two dimensional graphene, or a combination thereof.

14. The microchip detection and separation device recited in claim 11, wherein the sensor has a surface area of about 10 µm$^2$ to about 100 µm$^2$.

15. The microchip detection and separation device recited in claim 11, wherein the microchip is not larger than one square millimeter.

16. The microchip detection and separation device recited in claim 11, wherein the sensor is included in a detector further comprising at least one conductivity measuring device.

17. The microchip detection and separation device recited in claim 16, wherein the conductivity measuring device is a surface acoustical wave measuring device.

18. The microchip detection and separation device recited in claim 16, wherein the conductivity measuring device is a nano-mechanical resonator measuring device.

19. A method for detecting and separating components of a sample having multiple individual components, the method comprising:
  transporting a sample through a separation device having at least one inlet configured to receive the sample and at least one outlet configured to permit outflow of the multiple individual components of the sample from the separation device;
  impinging the multiple individual components of the sample onto at least one sensor configured to detect individual components of the sample, the at least one sensor including at least one channel formed in at least one material selected from the group consisting of a two dimensional material, a substantially two dimensional material, and combinations thereof;
  the sensor sensing a property which changes at least 3% when the material is exposed to a component forming not more than about one pico gram of the sample; and
  the sensor sensing a property which will change at least 3% when the material is exposed to a component forming not more than about 3 ppb of the sample.

20. The method of claim 19 wherein individual components which are detected and separated do not form more than about $10^{-21}$ gram of the sample.

21. The method of claim 19, wherein the separation device is a microchip and wherein the method comprises transporting the multiple individual components to a detector which includes the sensor, the detector including one or both of a conductivity measuring device or a nano-mechanical resonator measuring device.

22. The method of claim 19, wherein the material is selected from the group consisting of two dimensional or substantially two dimensional graphene, two dimensional or substantially two dimensional graphene oxide, two dimensional or substantially two dimensional boron nitride, two dimensional or substantially two dimensional molybdenum disulfide, and combinations thereof.

23. The method of claim 19, wherein the transporting the sample through the separation device comprises transporting the sample through sensor having a surface area of about 10 µm$^2$ to about 100 µm$^2$.

24. The method of claim 19, further comprising the sensor detecting multiple ones of the multiple individual components of the sample and detecting at least one of the individual components which forms not more than about $10^{-21}$ grams of an individual component of the sample.

* * * * *